May 8, 1956 C. E. SULLIVAN Plant Pat. 1,475
WALNUT TREE
Filed March 22, 1955
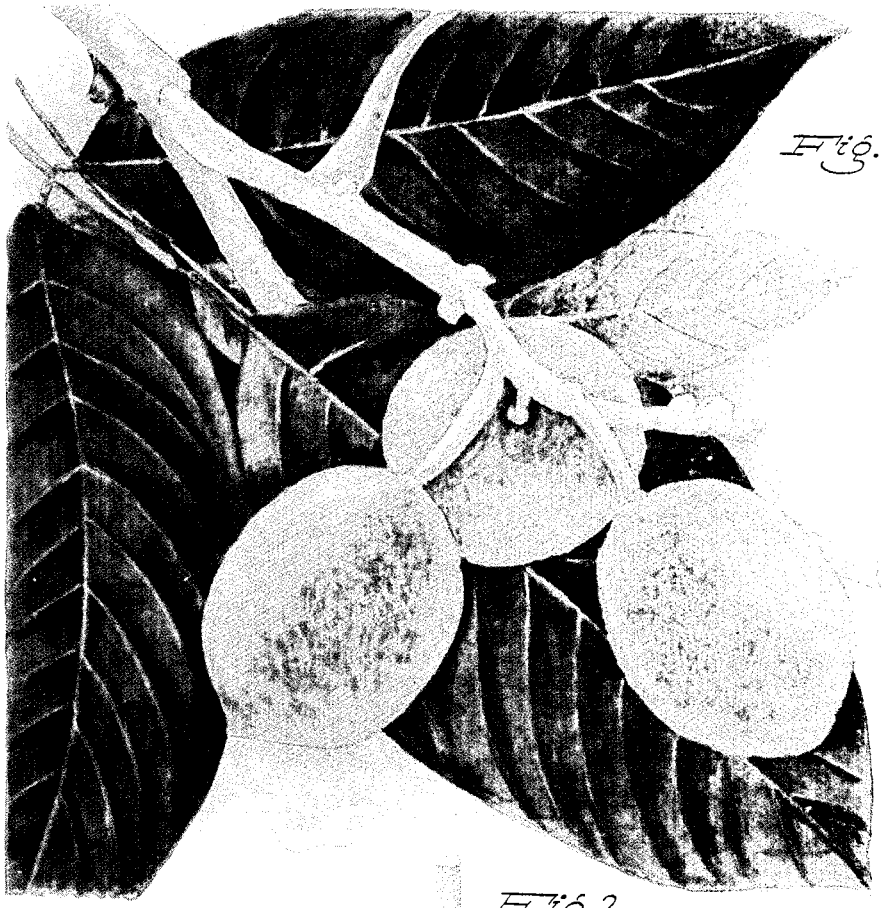
Fig. 1
Fig. 2
Fig. 3
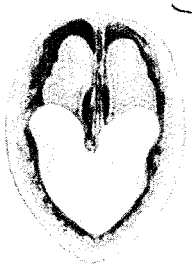
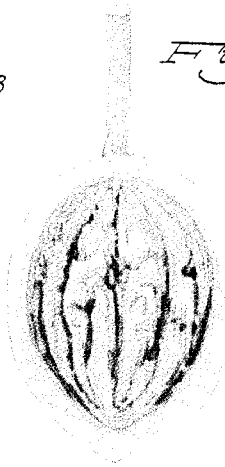
Fig. 4
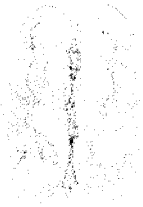
WITNESS
Addison E. Avery
INVENTOR
Charles Edward Sullivan
Webster & Webster
ATTYS.

United States Patent Office

Plant Pat. 1,475
Patented May 8, 1956

1,475

WALNUT TREE

Charles Edward Sullivan, Yuba City, Calif.

Application March 22, 1955, Serial No. 496,088

1 Claim. (Cl. 47—62)

This invention relates to a new and distinct variety of walnut tree which bears highly commercially valuable nuts; the variety having been originated by me, on my ranch near Yuba City, Sutter County, California, as a seedling of which the seed parent was the Payne walnut.

In originating the variety I planted a large number of selected nuts which had resulted from an open-pollinated cross of other varieties with the seed parent; the cross—as far as is known—having been Payne×probably Hartley, possibly some Eureka.

The original tree of the instant variety is a seedling from such planting. When the seedling, which was maintained under careful observation, grew to maturity it was recognized as having certain very distinctive characteristics, and was found to be especially suited for commercial growing.

I therefore selected such seedling for reproduction; asexual reproduction having been accomplished by patch-budding of the variety on several orchard blocks of Paradox Hybrid seedlings on my ranch located as aforesaid. These reproductions were found to carry forward all of the characteristics of the original seedling.

The present variety of walnut is distinctively advantageous in the following respects:

In comparison to the Franquette walnut—the leading variety in acreage in California, which variety does not come into substantial bearing until the ninth to tenth years—the present variety is characterized by heavy production, beginning when the tree is in a relatively early year of growth; one tree having produced forty-six pounds of nuts in its sixth year.

In comparison to the Hartley walnut—which is the best commercial walnut heretofore grown in California—the instant variety comes into bearing in an earlier year of growth just as in comparison to the Franquette walnut; and additionally—as to said Hartley walnut—bears heavier and the nuts are of better quality, being large in size and of attractive appearance. The nuts here are especially well filled, averaging 53% meat to shell by weight, whereas the Hartley walnut averages 43% when grown under the same soil and climatic conditions. As the trend is more and more toward commercially shelled nuts for the market, the above increase in the proportionate weight of the meat to the shell is of substantial value.

Also, the nuts of the present variety, while being large in size as aforesaid—averaging 99% large and 1% medium—consistently have meat of the highest market quality.

Still another feature of the present variety is that the nuts crack-out readily, with a large percentage of whole meats.

Another feature of the present variety of walnut is that the foliage leafs out late in spring, approximately two weeks later than the Payne walnut and just ahead of the Hartley walnut, allowing it to escape most of the spring rains and frost that do so much damage, particularly to the Payne walnut.

Still another feature is that the present variety harvests in mid-season in the fall; i. e. midway between said Payne and Hartley walnuts; thus coming off the tree ahead of the fall rains, as is desirable.

As far as is known none of the mentioned previously existent varieties of walnuts are patented.

In the drawings:

Fig. 1 is an elevation showing a cluster of the walnuts, together with twigs and leaves.

Fig. 2 is an elevation of one of the nuts in the hull; the latter being half cut away.

Fig. 3 is an elevation of one-half of a shell with the corresponding portion of the kernel remaining therein.

Fig. 4 is an elevation of the kernel removed from the shell.

Referring now more specifically to the botanical details of this new and distinct variety of walnut tree, the following is an outline description thereof; all major color plate identifications being by reference to Maerz and Paul Dictionary of Color:

Tree:

*Growing habit.*—Vigorous upright growth.

*Adaptability.*—Tree is adaptable to the common types of soil in which walnuts thrive.

*Productivity.*—Highly prolific, producing large quantities of high quality nuts.

Trunk: Medium to light colored; slightly rough; strong; vigorous.

Branches: Central leader upright. Strong side limbs. Medium to light at trunk, turning to brown at tips.

*Twigs.*—On laterals throughout tree. Long.

Foliage: Moderate to heavy.

Disease resistance: Relatively resistant to blight and sunburn, even in the hot climate of the interior valleys of California. These characteristics were ascertained by observing a tree of the present variety growing in an orchard block along with a number of standard walnut varieties, including the Payne; all of the trees having been subject to the same conditions of culture, irrigation, fertilization, and climate. By observation, and by crack tests of the crops of the varieties in such orchard block, the instant variety proved substantially less susceptible to blight and sunburn, and particularly with respect to the Payne variety.

Buds: Hardy; medium size; plump; numerous double buds.

Form: Upright; inverted cone shape.

Leaves:

*Form.*—Lanceolate; pointed at tip; curled slightly on edges; medium size.

*Petiole.*—Very short; strong; stiff.

*Glands.*—None.

*Color.*—Top side—medium to dark green (shading from 22–L–9). Under side—lighter green (22–K–6). Pronounced yellow veins (19–K–1).

Nuts:

*Quality.*—Exceptionally good.

*Maturity.*—Mid-season (October). Harvest approximately midway between Payne walnut and Hartley walnut.

*Tenacity.*—Tenacious to fruiting wood until hulls split, then nuts fall readily on shaking.

*Cluster.*—Substantially all nuts in pairs or clusters of three.

*Size.*—Large. Average grading—99% large, 1% medium.

*Weight.*—Nut is well filled with meat, averaging 53% meat to shell by weight.

*Base.*—Small. Rounded, expanding to broadest point two-thirds way up nut.

*Point.*—Rounded top, small sharp pointed apex.

*Shell.*—Heavy; well sealed; handles good. Color—Light brown (13–F–6), shading to darker brown (7–C–10).

*Hull.*—Medium thickness. Outside color—Light green (21–J–1), spotted or mottled lighter green (19–I–1). Flesh color—Light yellowish green (19–K–1).

*Kernel or meat.*—Exceptionally good flavor. Kernel halves parallel or symmetrical in shape. Outside color—Light brown (12–1–6) shading to darker brown (7–A–12), clear of speckles and spots. Flesh color—Ivory (9–B–1). Size—Large, kernel substantially filling shell; cracks out easily with a large percentage remaining whole.

The tree and its nuts herein described may vary in slight detail due to climatic and soil conditions under which the variety may be grown.

None of the prior varieties of walnuts mentioned herein are patented.

Having thus described my invention, I claim:

A new and distinct variety of walnut tree, substantially as illustrated and described, characterized—in comparison to the Hartley and Franquette walnuts by the beginning of production of nuts in a relatively early year of growth and at least by the sixth year thereof; and further characterized—especially in comparison to said Hartley walnut—by the heavier bearing of nuts which are large, well filled, of better quality, and attractive appearance; and additionally characterized by nuts which are relatively free from blight and sunburn and which crack-out readily, by foliage which leafs out late in spring, approximately two weeks later than the Payne walnut and just ahead of the Hartley walnut, and by a mid-season harvest in the fall between said Payne and Hartley walnuts.

No references cited.